US006725072B2

(12) United States Patent
Steuer et al.

(10) Patent No.: US 6,725,072 B2
(45) Date of Patent: Apr. 20, 2004

(54) SENSOR FOR TRANSCUTANEOUS MEASUREMENT OF VASCULAR ACCESS BLOOD FLOW

(75) Inventors: Robert R. Steuer, Pleasant View, UT (US); David A. Bell, Farmington, UT (US); David R. Miller, Morgan, UT (US)

(73) Assignee: Hema Metrics, Inc., Kaysville, UT (US)

(*) Notice: Subject to any disclaimer, the term of this patent is extended or adjusted under 35 U.S.C. 154(b) by 231 days.

(21) Appl. No.: 09/750,076

(22) Filed: Dec. 29, 2000

(65) Prior Publication Data

US 2001/0003793 A1 Jun. 14, 2001

Related U.S. Application Data

(63) Continuation-in-part of application No. 09/244,756, filed on Feb. 5, 1999, now Pat. No. 6,181,958, which is a continuation-in-part of application No. 09/084,958, filed on May 28, 1998, now Pat. No. 6,266,546, which is a continuation of application No. 08/479,352, filed on Jun. 7, 1995, now Pat. No. 5,803,908, which is a continuation of application No. 08/317,726, filed on Oct. 4, 1994, now Pat. No. 5,499,627, which is a division of application No. 08/011,882, filed on Feb. 1, 1993, now Pat. No. 5,372,136, which is a continuation of application No. 07/598,169, filed on Oct. 16, 1990, now abandoned.

(60) Provisional application No. 60/073,784, filed on Feb. 5, 1998.

(51) Int. Cl.[7] .................................................. A61B 5/00

(52) U.S. Cl. ....................................... 600/310; 600/322

(58) Field of Search ................................. 600/316, 322, 600/323, 344, 437–454, 504; 356/39–42

(56) References Cited

U.S. PATENT DOCUMENTS

| 3,638,640 A | | 2/1972 | Shaw |
| 3,880,151 A | | 4/1975 | Nilsson et al. |
| 3,998,550 A | * | 12/1976 | Konishi et al. ............. 600/310 |

(List continued on next page.)

FOREIGN PATENT DOCUMENTS

| EP | 104772 B1 | 4/1984 |
| EP | 160768 B1 | 11/1985 |
| EP | 0 529 412 | 3/1993 |
| EP | 0 928 614 | 7/1999 |
| WO | WO 86/06946 | 12/1986 |
| WO | WO 89/01758 | 3/1989 |
| WO | WO 93/06456 | 4/1993 |

OTHER PUBLICATIONS

J.P. Payne and J.W. Severinghaus, Eds., *Pulse Oximetry*, Chapters 1 and 2 (®1986).

(List continued on next page.)

*Primary Examiner*—Max F. Hindenburg
*Assistant Examiner*—David J. McCrosky
(74) *Attorney, Agent, or Firm*—Jacobson Holman PLLC

(57) ABSTRACT

An optical sensor includes photoemitter and photodetector elements at multiple spacings ($d_1$, $d_2$) for the purpose of measuring the bulk absorptivity ($\alpha$) of an area immediately surrounding and including a hemodialysis access site, and the absorptivity ($\alpha_o$) of the tissue itself. At least one photoemitter element and at least one photodetector element are provided, the total number of photoemitter and photodetector elements being at least three. The photoemitter and photodetector elements are collinear and alternatingly arranged, thereby allowing the direct transcutaneous determination of vascular access blood flow.

13 Claims, 8 Drawing Sheets

U.S. PATENT DOCUMENTS

| | | | |
|---|---|---|---|
| 4,014,321 | A | 3/1977 | March |
| 4,081,372 | A | 3/1978 | Atkin et al. |
| 4,086,915 | A | 5/1978 | Kofsky et al. |
| 4,167,331 | A | 9/1979 | Nielsen |
| 4,181,610 | A | 1/1980 | Shintani et al. |
| 4,223,680 | A | 9/1980 | Jöbsis |
| 4,266,554 | A | 5/1981 | Hamaguri |
| 4,295,470 | A | 10/1981 | Shaw et al. |
| 4,416,285 | A | 11/1983 | Shaw et al. |
| 4,446,871 | A | 5/1984 | Imura |
| 4,653,498 | A | 3/1987 | New, Jr. et al. |
| 4,655,225 | A | 4/1987 | Dahne et al. |
| 4,685,464 | A | 8/1987 | Goldberger et al. |
| 4,714,080 | A | 12/1987 | Edgar, Jr. et al. |
| 4,770,179 | A | 9/1988 | New, Jr. et al. |
| 4,805,623 | A | 2/1989 | Jöbsis |
| 4,819,752 | A | 4/1989 | Zelin |
| 4,821,734 | A | 4/1989 | Koshino |
| 4,824,242 | A | 4/1989 | Frick et al. |
| 4,825,872 | A | 5/1989 | Tan et al. |
| 4,825,879 | A | 5/1989 | Tan et al. |
| 4,832,484 | A | 5/1989 | Aoyagi et al. |
| 4,863,265 | A | 9/1989 | Flower et al. |
| 4,867,557 | A | 9/1989 | Takatani et al. |
| 4,920,972 | A | 5/1990 | Frank et al. |
| 4,925,299 | A | 5/1990 | Meisberger et al. |
| 5,028,787 | A | 7/1991 | Rosenthal et al. |
| 5,035,243 | A | 7/1991 | Muz |
| 5,048,524 | A | 9/1991 | Bailey |
| 5,054,487 | A | 10/1991 | Clarke |
| 5,057,695 | A | 10/1991 | Hirao et al. |
| 5,058,587 | A | 10/1991 | Kohno et al. |
| 5,059,394 | A | 10/1991 | Phillips et al. |
| 5,066,859 | A | 11/1991 | Karkar et al. |
| 5,092,836 | A | 3/1992 | Polaschegg |
| 5,101,825 | A | 4/1992 | Gravenstein et al. |
| 5,111,817 | A | 5/1992 | Clark et al. |
| 5,127,406 | A | 7/1992 | Yamaguchi |
| 5,137,023 | A | 8/1992 | Mendelson et al. |
| 5,158,091 | A | 10/1992 | Butterfield et al. |
| 5,193,543 | A | 3/1993 | Yelderman |
| 5,237,999 | A | 8/1993 | von Berg |
| 5,285,783 | A | * 2/1994 | Secker ................... 600/323 |
| 5,351,686 | A | 10/1994 | Steuer et al. |
| 5,456,253 | A | 10/1995 | Steuer et al. |
| 5,499,627 | A | 3/1996 | Steuer et al. |
| 5,520,177 | A | 5/1996 | Ogawa et al. |
| 5,551,422 | A | * 9/1996 | Simonsen et al. .......... 600/322 |
| 5,595,182 | A | 1/1997 | Krivitski |
| 5,785,657 | A | * 7/1998 | Breyer et al. ............ 600/454 |
| 5,797,841 | A | * 8/1998 | Delonzor et al. .......... 600/344 |
| 5,803,908 | A | 9/1998 | Steuer et al. |
| 5,817,009 | A | 10/1998 | Rosenheimer et al. |
| 5,974,337 | A | 10/1999 | Kaffka et al. |
| 6,041,246 | A | 3/2000 | Krivitski et al. |
| 6,117,099 | A | 9/2000 | Steuer et al. |
| 6,153,109 | A | 11/2000 | Krivitski |
| 6,167,765 | B1 | 1/2001 | Weitzel |
| 6,189,388 | B1 | 2/2001 | Cole et al. |
| 6,210,591 | B1 | 4/2001 | Krivitski |
| 6,452,371 | B1 | 9/2002 | Brugger |

OTHER PUBLICATIONS

John D. Bower and Thomas G. Coleman, *Circulatory Function During Chronic Hemodialysis*, vol. XV Trans. Amer. Soc. Artif. Int. Organs, 1969, 373–377.

Larry Reynolds, C. Johnson, A. Ishimaru, "Diffuse reflectance from a finite blood medium: applications to the modeling of fiber optic catheters," Sep. 1976, vol. 15, No. 9, *Applied Optics*, pp. 2059–2067.

R.N. Greenwood, C, Aldridge, L. Goldstein, L.R.I. Baker and W.R. Cattell, "Assessment of arteriovenous fistulae from pressure and thermal dilution studies: clinical experience in forearm fistulae," *Clinical Nephrology*, vol. 23, No. 4–1985, pp. 189–197.

R.N. Greenwood, C. Aldridge and W.R. Cattell, "Serial blood water estimations and in–line blood viscometry: the continuous measurement of blood volume during dialysis procedures," *Clinical Science* (1984)66, pp. 575–583.

C. Aldridge, R.N. Greenwood, W.R. Cattell and R.V. Barrett, "The assessment of arteriovenous fistulae created for haemodialysis from pressure and thermal dilution measurements," *Journal of Medical Engineering & Technology*, vol. 8, No. 3, (May/Jun.), pp. 118–124.

L. Goldstein, L. Pavitt, R.N. Greenwood, C. Aldridge, L.R.I. Baker and W.R. Cattell, "The Assessment of Areteriovenous Fistulae From Pressure and Recirculation Studies," *ProcEDTNA–ERCA* (1985) vol. 14., pp. 207–215.

R.N. Greenwood, C. Aldridge, L. Goldstein, L.R.I. Baker and W.R. Cattell, "Assessment of Arteriovenous Fistulas From Pressure and Recirculation Studies: Clinical Experience In 215 Upper Limb Fistulas," *ProcEDTA–ERA* (1985), vol. 22, pp. 296–302.

Joseph M. Schmitt, James D. Meindl and Frederick G. Mihm, "An Integrated Circuit–Based Optical Sensor for In Vivo Measurement of Blood Oxygenation," *IEEE Transactions On Biomedical Engineering*, vol. BME–33, No. 21, Feb. 1986, pp. 98–107.

Joseph M. Schmitt, Fred G. Mihm and James Meindl, *New Methods for Whole Blood Oximetry*, Annals of Biomedical Engineering, vol., 14, pp. 35–52, 1986.

Mark R. Arnfield, J. Tulip and Malcolm McPhee, "Optical Propagation in Tissue With Anisotropic Scattering," *IEEE Transactions on Biomedical Engineering*, vol. 35, No. 5, May 1988, pp. 372–381.

N.M. Krivitski, "Theory and validation of access flow measurements by dilution technique during hemodialysis," *Kidney Int* 48:244–250, 1995.

N.M. Krivitski, "Novel method to measure access flow during hemodialysis by ultrasound velocity dilution technique," *ASAIO J* 41:M741–M745, 1995.

T.A. Depner and N.M. Krivitski, "Clinical measurement of blood flow in hemodialysis access fistulae and grafts by ultrasound dilution," *ASAIO J* 41:M745–M749, 1995).

D. Yarar et al., "Ultrafiltration method for measuring vascular access flow rates during hemodialysis," *Kidney Int.*, 56: 1129–1135 (1999).

N.M. Krivitski et al., "Saline Release Method to Measure Access Flow (AF) by Ultrasound Dilution during Hemodialysis," *JASN Abstracts*, 8:164A, 1997.

* cited by examiner

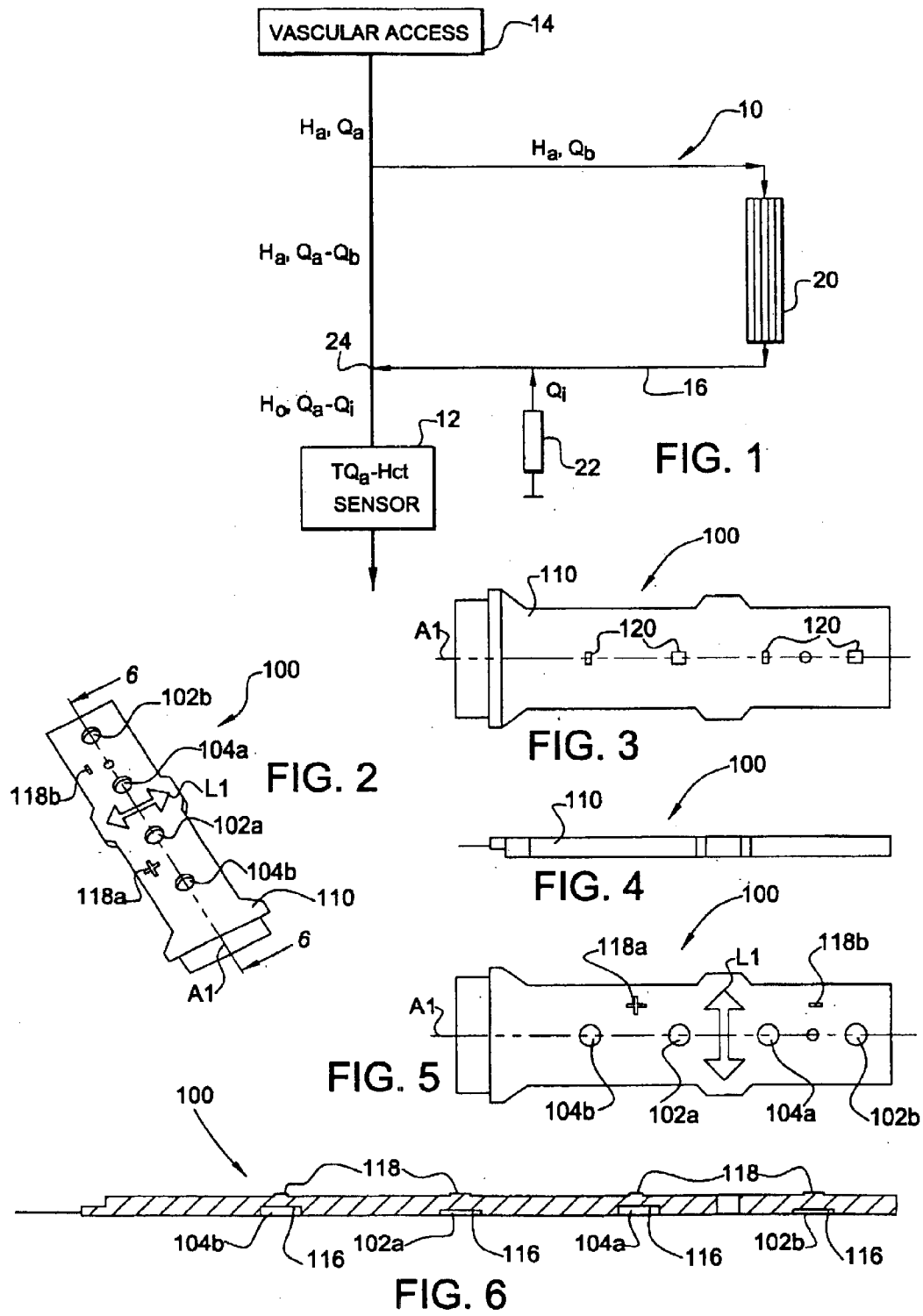

SENSOR FOR TRANSCUTANEOUS MEASUREMENT OF VASCULAR ACCESS BLOOD FLOW

CROSS-REFERENCE TO RELATED APPLICATIONS

The present patent application is a continuation-in-part of application Ser. No. 09/084,958, filed May 28, 1998 (now U.S. Pat. No. 6,266,546), which is a continuation of application Ser. No. 08/479,352, filed Jun. 7, 1995 (now U.S. Pat. No. 5,803,908), which is a continuation of application Ser. No. 08/3 17,726, filed Oct. 4, 1994 (now U.S. Pat. No. 5,499,627), which is a divisional of application Ser. No. 08/011,882, filed Feb. 1, 1993 (now U.S. Pat. No. 5,372,136), which is a continuation of application Ser. No. 07/598,169, filed Oct. 16, 1990 (abandoned); and a continuation-in-part of application Ser. No. 09/244,756, filed Feb. 5, 1999 (now U.S. Pat. No. 6,181,958), which claims the benefit of Provisional Application No. 60/073,784, filed Feb. 5, 1998), all of which are incorporated herein by reference in their entireties.

BACKGROUND OF THE INVENTION

1. Field of the Invention

The present invention relates to apparatus for non-invasively measuring one or more blood parameters. More specifically, the invention relates to apparatus for the transcutaneous measurement of vascular access blood flow. The invention can also be used for precise access location, as a "flow finder," and also can be used to locate grafts and to localize veins in normal patients for more efficient canulatization.

2. Related Art

Routine determination of the rate of blood flow within the vascular access site during maintenance hemodialysis is currently considered an integral component of vascular access assessment. While the relative importance of vascular access flow rates and venous pressure measurements in detecting venous stenoses is still somewhat controversial, both the magnitude and the rate of decrease in vascular access flow rate have been previously shown to predict venous stenoses and access site failure. The traditional approach for determining the vascular access flow rate is by Doppler flow imaging; however, these procedures are expensive and cannot be performed during routine hemodialysis, and the results from this approach are dependent on the machine and operator.

Determination of the vascular access flow rate can also be accurately determined using indicator dilution methods. Early indicator dilution studies determined the vascular access flow rate by injecting cardiogreen or radiolabeled substances at a constant rate into the arterial end of the access site and calculated the vascular access flow rate from the steady state downstream concentration of the injected substance. These early attempts to use indicator dilution methods were limited to research applications since this approach could not be routinely performed during clinical hemodialysis. It has long been known that in order to determine the vascular access flow (ABF) rate during the hemodialysis procedure, the dialysis blood lines can be reversed (by switching the arterial and venous connections) to direct the blood flow within the hemodialysis circuit in order to facilitate the injection of an indicator in the arterial end of the access site and detect its concentration downstream (N. M. Krivitski, "Theory and validation of access flow measurements by dilution technique during hemodialysis," Kidney Int 48: 244–250, 1995; N. M. Krivitski, "Novel method to measure access flow during hemodialysis by ultrasound velocity dilution technique," ASAIO J 41: M741–M745, 1995; and T. A. Depner and N. M. Krivitski, "Clinical measurement of blood flow in hemodialysis access fistulae and grafts by ultrasound dilution," ASAIO J 41: M745–M749, 1995)). D. Yarar et al., Kidney Int., 65: 1129–1135 (1999), developed a similar method using change in hematocrit to determine ABF. Various modifications of this approach have been subsequently developed. While these latter indicator dilution methods permit determination of the vascular access flow rate during routine hemodialysis, reversal of the dialysis blood lines from their normal configuration is inconvenient and time-consuming since it requires that the dialyzer blood pump be stopped and the dialysis procedure is relatively inefficient during the evaluation of the flow rate which can take up to twenty minutes. Furthermore, some of these indicator dilution methods also require accurate determination of the blood flow rate.

Clinical usefulness and ease of use are major developmental criteria. From a routine clinical point of view the need to design a simple sensor, easily attached to the patient, requiring no line reversals, no knowledge of the dialysis blood flow rate, $Q_b$, and transcutaneously applied to skin, thereby accomplishing the measurement within a total of 1–2 minutes, is crucial to have repeated, routine meaningful ABF trend information, whereby access health is easily tracked.

SUMMARY OF THE INVENTION

It is therefore an object of the present invention to provide apparatus for non-invasively measuring one or more blood parameters.

It is another object of the present invention to provide an optical hematocrit sensor that can detect changes in hematocrit transcutaneously.

It is still another object of the invention to provide an optical hematocrit sensor that can be used to determine the vascular access flow rate within 2 minutes and without reversal of the dialysis blood lines or knowledge of $Q_b$, all transcutaneously.

These and other objects of the invention are achieved by the provision of an optical sensor including complementary emitter and detector elements at multiple spacings ($d_1$, $d_2$) for the purpose of measuring the bulk absorptivity ($\alpha$) of the volume immediately surrounding and including the access site, and the absorptivity ($\alpha_o$) of the tissue itself.

In one aspect of the invention, the optical sensor system comprises an LED of specific wavelength and a complementary photodetector. A wavelength of 805 nm–880 nm, which is near the known isobestic wavelength for hemoglobin, is used.

When the sensor is placed on the surface of the skin, the LED illuminates a volume of tissue, and a small fraction of the light absorbed and back-scattered by the media is detected by the photodetector. The illuminated volume as seen by the photodetector can be visualized as an isointensity ellipsoid, as individual photons of light are continuously scattered and absorbed by the media. Because a wavelength of 805 nm–880 nm is used, hemoglobin of the blood within the tissue volume is the principal absorbing substance. The scattering and absorbing characteristics are mathematically expressed in terms of a bulk attenuation coefficient ($\alpha$) that is specific to the illuminated media. The amount of light detected by the photodetector is proportional via a modified Beer's law formula to the instantaneous net $\alpha$ value of the media.

When the volume of tissue illuminated includes all or even part of the access, the resultant α value includes information about both the surrounding tissue and the access itself. In order to resolve the signal due to blood flowing within the access from that due to the surrounding tissues, the sensor system illuminates adjacent tissue regions on either side of the access. Values of $\alpha_o$ for tissue regions not containing the access are then used to normalize the signal, thus providing a baseline from which relative changes in access hematocrit can be assessed.

Other objects, features and advantages of the present invention will be apparent to those skilled in the art upon a reading of this specification including the accompanying drawings.

BRIEF DESCRIPTION OF THE DRAWINGS

The invention is better understood by reading the following Detailed Description of the Preferred Embodiments with reference to the accompanying drawing figures, in which like reference numerals refer to like elements throughout, and in which:

FIG. 1 is a diagrammatic view of a dialysis circuit in which a $TQ_a$ hematocrit sensor in accordance with the present invention is placed at the hemodialysis vascular access site.

FIG. 2 is a perspective view of a first embodiment of a $TQ_a$ hematocrit sensor in accordance with the present invention.

FIG. 3 is a bottom plan view of the $TQ_a$ hematocrit sensor of FIG. 2.

FIG. 4 is a side elevational view of the $TQ_a$ hematocrit sensor of FIG. 2.

FIG. 5 is a top plan view of the $TQ_a$ hematocrit sensor of FIG. 2.

FIG. 6 is a cross-sectional view taken along line 6—6 of FIG. 2.

DETAILED DESCRIPTION OF THE PREFERRED EMBODIMENTS

Figure 7:
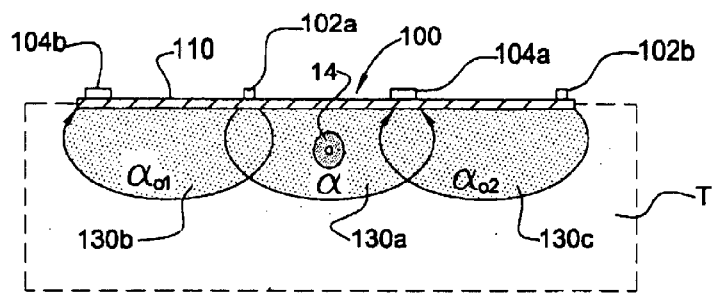
FIG. 7 is a diagrammatic view illustrating the $TQ_a$ sensor of FIG. 2 and the illuminated volumes or "glowballs" produced by the emitters and seen by the detectors thereof.
Figures 8, 9, 10:
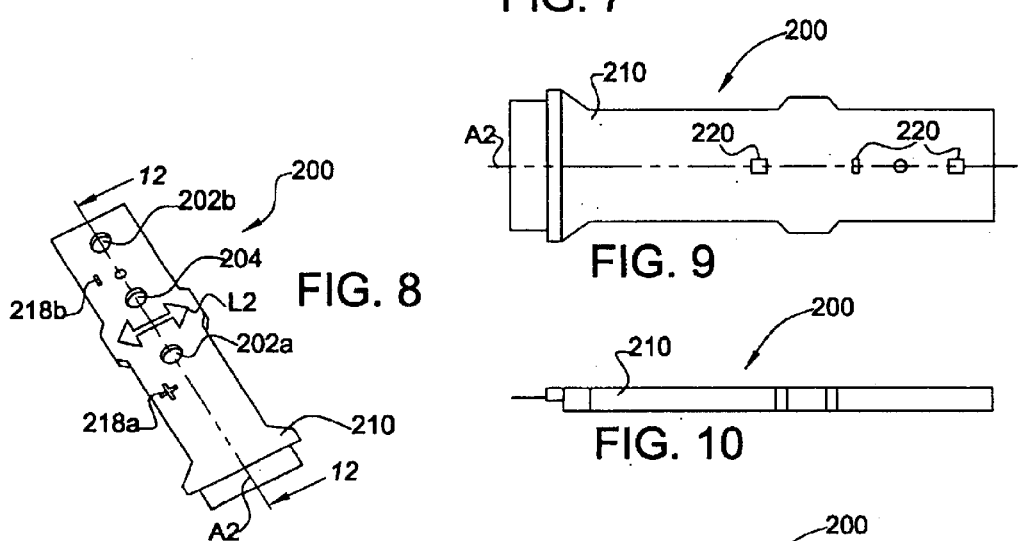
FIG. 8 is a perspective view of a second embodiment of a $TQ_a$ hematocrit sensor in accordance with the present invention.
FIG. 9 is a bottom plan view of the $TQ_a$ hematocrit sensor of FIG. 8.
FIG. 10 is a side elevational view of the $TQ_a$ hematocrit sensor of FIG. 8.
Figure 11:
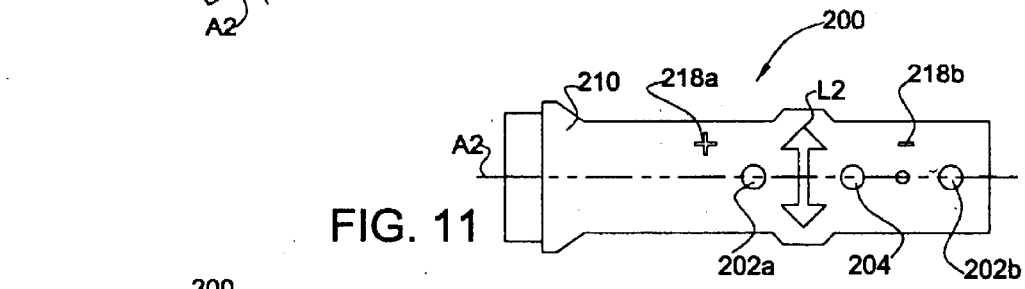
FIG. 11 is a top plan view of the $TQ_a$ hematocrit sensor of FIG. 8.
Figure 12:
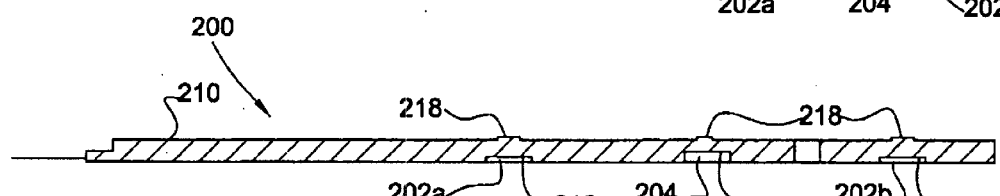
FIG. 12 is a cross-sectional view taken along line 12—12 of FIG. 9.

In describing preferred embodiments of the present invention illustrated in the drawings, specific terminology is employed for the sake of clarity. However, the invention is not intended to be limited to the specific terminology so selected, and it is to be understood that each specific element includes all technical equivalents that operate in a similar manner to accomplish a similar purpose.

The following abbreviations and variables are used throughout the present disclosure in connection with the present invention:

α=access site optical attenuation coefficient
$\alpha_o$=non-access site optical attenuation coefficient
$B_o$=composite of all the non-access region S, K coefficients
C=proportionality scalar
CPR=cardio-pulmonary recirculation
d=distance between the emitter and the detector
H=hematocrit, generally
$H_a$=hematocrit within the vascular access site $H_{ao}$=hematocrit beneath the sensor (outside the dialyzer)
ΔH=change in hematocrit ($H_a$–$H_{ao}$)
i=intensity of light, generally
$I_{baseline}$=baseline intensity (taken in the absence of a bolus)
$I_{measured}$=light back-scattered from a turbid tissue sample
$I_o$=emitter radiation intensity
K=bulk absorption coefficient
$K_b$=access site blood coefficient
$Q_a$=vascular access blood flow rate
$Q_b$=dialyzer blood flow rate
$Q_f$=dialyzer ultrafiltration rate
$Q_i$=average injection inflow rate
S=bulk scattering coefficient
SD=standard deviation
SNR=signal-to-noise ratio
t=time (measured from time of injection)
$TQ_a$=transcutaneous access blood flow
V=known volume of saline injected into dialysis venous line
$X_b$=percentage of the access volume to the total volume illuminated (access blood proration value)
$X_o$=percentage of the non-access area to the total volume The optical hematocrit sensor in accordance with the present invention comprises a light emitting source (emitter) (preferably an LED of specific wavelength) and a complementary photodetector that can be placed directly on the skin over a vascular access site. The LED preferably emits light at a wavelength of 805 nm–880 nm, because it is near the known isobestic wavelength for hemoglobin, is commercially available, and has been shown to be effective in the optical determination of whole blood parameters such as hematocrit and oxygen saturation.

When the sensor is placed on the surface of the skin, the LED illuminates a volume of tissue, and a small fraction of the light absorbed and back-scattered by the media is detected by the photodetector. While light travels in a straight line, the illuminated volume as seen by the photodetector can be visualized as an isointensity ellipsoid, as individual photons of light are continuously scattered and absorbed by the media. Because a wavelength of 805 nm–880 nm is used, hemoglobin of the blood within the tissue volume is the principal absorbing substance. The scattering and absorbing characteristics are mathematically expressed in terms of a bulk attenuation coefficient (α) that is specific to the illuminated media. The amount of light detected by the photodetector is proportional via a modified Beer's law formula to the instantaneous net α value of the media.

When the volume of tissue illuminated includes all or even part of the access, the resultant α value includes information about both the surrounding tissue and the access itself. In order to resolve the signal due to blood flowing within the access from that due to the surrounding tissues, the sensor system illuminates adjacent tissue regions on either side of the access. Values of $α_o$ for tissue regions not containing the access are then used to normalize the signal, thus providing a baseline from which relative changes can be assessed in access hematocrit in the access blood flowing directly under the skin.

FIG. 1 illustrates a dialysis circuit in which a $TQ_a$ hematocrit sensor 12 in accordance with the present invention is placed over the hemodialysis vascular access site 14, with the dialysis arterial and venous blood lines 16a and 16b in the normal configuration, for measuring $TQ_a$. A dialyzer 20 downstream of the vascular access site 14 and a syringe 22 for injecting a reference diluent (for example, saline) downstream of the dialyzer 20 are indicated. The hematocrits and flow rates under steady state conditions are also indicated, where $Q_a$ is the access flow rate, $Q_b$ is the dialyzer blood flow rate, $Q_i$ is the injection flow rate, $H_a$ is the hematocrit in the access flow, and $H_o$ is the hematocrit at the sensor 12. The hematocrit sensor 12 is placed directly on the skin over the vascular access site 14 downstream of the venous dialysis needle 24.

Figure 35:
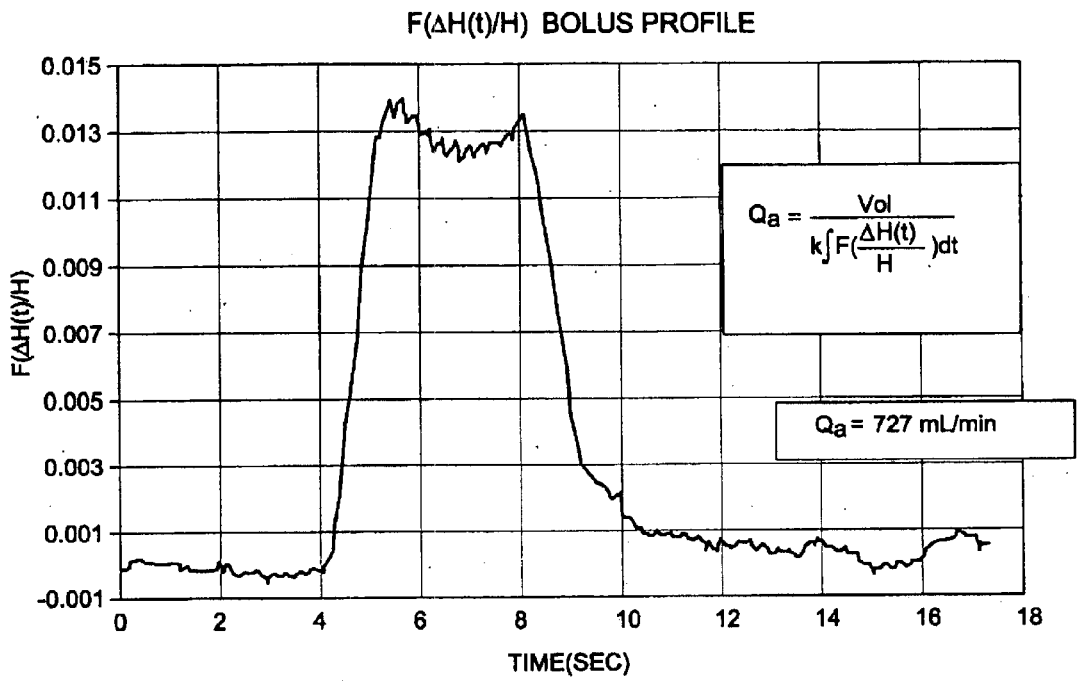
FIG. 35 is a graphical representation of a signal proportional to the hematocrit in the vascular access as recorded by a sensor and associated monitoring system in accordance with the invention.

As shown in FIG. 35, the sensor 12 and an associated monitoring system 30 records a signal proportional to the hematocrit in the vascular access site 14 ($H_a$). The monitoring system 30 can be a computer including a computer processor and memory, and output means such as a video monitor and printer (not shown). After a stable $H_a$ value is obtained, a known volume (V) of normal saline is injected via the syringe 22 into the dialysis venous line 16b, which reduces the hematocrit beneath the sensor 12 to a time-dependent hematocrit $H_o$ during the injection.

Derivation of the equation used to calculate the vascular access flow rate when using the bolus injection indicator dilution approach is complex. However, the constant infusion and bolus injection indicator dilution approaches yield identical results; therefore, the governing equation was derived from steady state constant infusion principles. Consider the dialysis circuit in FIG. 1 where a steady infusion of saline occurs in the dialysis venous blood line 16b (ultrafiltration at the dialyzer 20 is neglected). Red cell balance where the dialysis venous blood flow enters the access site 14 requires $$H_a(Q_a-Q_b)+H_aQ_b=H_o(Q_a+Q_i) \qquad (1)$$

Solving for $Q_a$, the vascular access flow rate, yields $$Q_a = \frac{Q_i}{\frac{\Delta H}{H_o}} \qquad (2)$$

where ΔH denotes $H_a$–$H_{ao}$. This equation describes the changes in hematocrit at the sensor 12 during a constant infusion of normal saline in the dialysis venous blood line 16b. (If ultrafiltration at the dialyzer 20 occurs at a rate of $Q_f$, then the numerator in this equation becomes $Q_i$–$Q_f$).

Noting that $Q_i$ is equivalent to the volume of saline injected in a specified time interval, equation (2) is therefore equivalent to:

$$Q_a = \frac{V}{\int F\left(\frac{\Delta H}{H}\right)(t)dt} \qquad (3)$$

to yield the vascular access flow rate ($Q_a$), where ΔH denotes $H_a$–$H_{ao}$ and the integral (area under the curve) in the above equation is from the time of injection (t=0) to where the signal has returned to the baseline value (t=∞). This equation is valid independent of the rate of saline injection or the dialyzer blood flow rate. The signals detected by the $TQ_a$ sensor 12 can be used to calculate $$F\left(\frac{\Delta H}{H_o}\right).$$

Determination of $$F\left(\frac{\Delta H}{H}\right)$$

The percentage change in blood parameters (both macroscopic and microscopic) passing through the access site 14 may be measured in a variety of ways. Macroscopic parameters such as bulk density or flow energy can be measured by ultrasonic, temperature, or conductivity means. Microscopic parameters (sometimes called "physiologic or intrinsic" parameters) such as hematocrit or red cell oxygen content are measured by optical means. Each technique has its respective advantages and disadvantages, both rely on the quantity $$\frac{\Delta H}{H}.$$

Inherent in all of these is the need to differentiate the access site 14, and parameter changes therein, from the surrounding tissue structure. The $TQ_a$ sensor 12 in accordance with the present invention is positioned directly over the access site region 14 itself approximately 25 mm downstream of the venous needle 24, and is based upon optical back-scattering of monochromatic light ($\lambda$=805 nm–880 nm) from the blood flow in the access site 14 and the surrounding tissues. The theory on which the construction of the $TQ_a$ sensor 12 is based requires the use of optical physics and laws associated with optical determination of physiologic elements including hematocrit.

Modified Beer's Law

Numerous studies have shown that light back-scattered from a turbid tissue sample follows a modified form of Beer's Law, $$I_{measured} = I_o A e^{-\alpha d} \qquad (4)$$

where $I_o$ is the radiation intensity emitted from the LED, A is a complex function of d and $\alpha$ of the various layers of tissue (epidermis, dermis, and subcutaneous tissue), d is the distance between the LED and detector, and $\alpha$ is the bulk optical attenuation coefficient. The $\alpha$ term is a function of the absorption and scattering nature of the tissue and has a strong dependence on hematocrit.

$$\alpha \approx \frac{-\text{Ln}\left(\frac{I_{measured}}{I_o}\right)}{d} \qquad (5)$$

Compartmentalization of $\alpha$

A transcutaneously measured $\alpha$ value is actually a pro-rated composite measure of all the absorption and scattering elements contained within the illuminated volume or "glow-ball" of the emitter source, and typically includes the effects of tissue, water, bone, blood, and in the case of hemodialysis patients, the access site 14. In the determination of $\alpha$, clearly only the blood flowing through the access site 14 is of interest. The task therefore becomes one of separating the effects of absorption and scattering of the access site 14 from that of surrounding tissue structure. Starting with the well known definition, $$\alpha = \sqrt{3K(K+S)} \qquad (6)$$

where K is the bulk absorption coefficient and S is the bulk scattering coefficient, and separating the access site 14 from non-access blood coefficients and rearranging terms, $$X_b K_b \approx \alpha^2 - B_o \qquad (7)$$

where $X_b$=ratio of the access volume to the total volume illuminated $K_b$=access blood coefficient $B_o$=composite of all the non-access region S and K coefficients Now, letting the non-access components become $\alpha_o^2 = B_o$, we have $$X_b K_b = \alpha^2 - \alpha_o^2 \qquad (8)$$

In equation (6), the access blood coefficient, $K_b$, is directly proportional to hematocrit (H), $K_b$=H·C. Therefore, $$X_b K_b = X_b \cdot H \cdot C = \alpha^2 - \alpha_o^2 \qquad (9)$$

where C is a proportionality scalar known from the literature or empirically derived.

Figure 13:
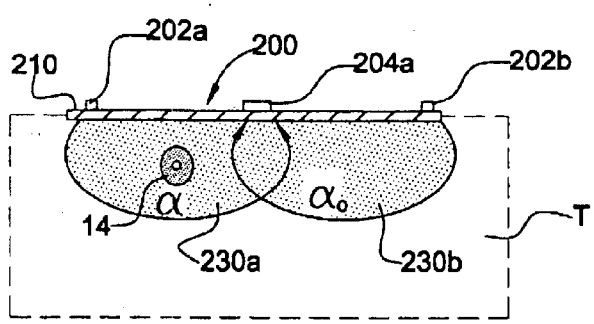
FIG. 13 is a diagrammatic view illustrating the $TQ_a$ hematocrit sensor of FIG. 8 and the illuminated volumes or "glowballs" produced by the emitters and seen by the detector thereof.
Figures 14, 15, 16, 17:
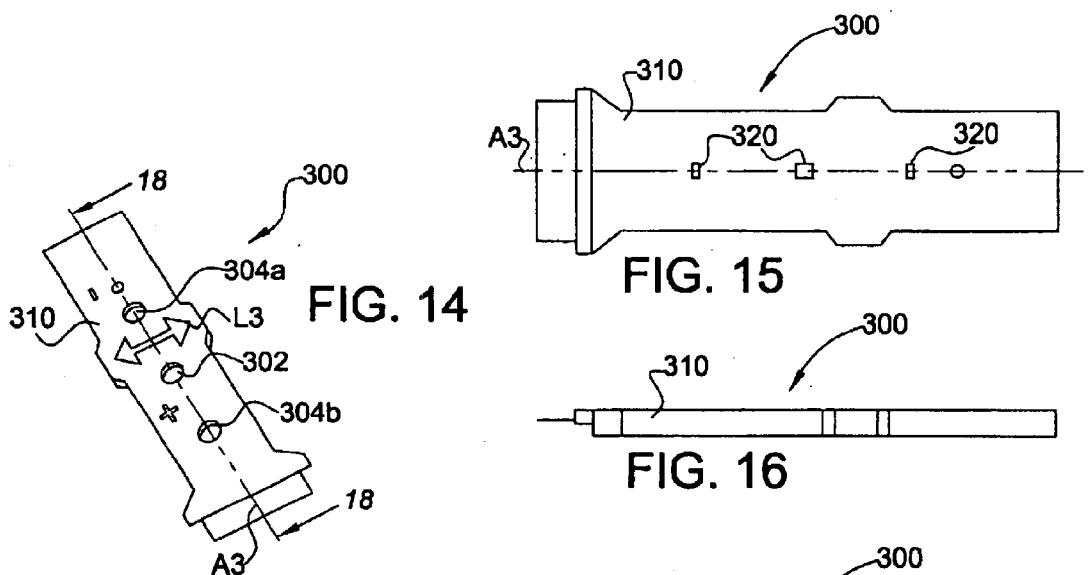
FIG. 14 is a perspective view of a third embodiment of a $TQ_a$ hematocrit sensor in accordance with the present invention.
FIG. 15 is a bottom plan view of the $TQ_a$ hematocrit sensor of FIG. 14.
FIG. 16 is a side elevational view of the $TQ_a$ hematocrit sensor of FIG. 14.
FIG. 17 is a top plan view of the $TQ_a$ hematocrit sensor of FIG. 14.
Figure 18:
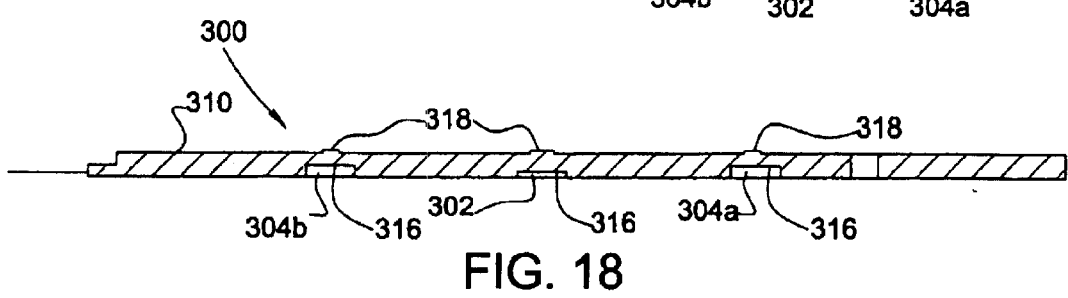
FIG. 18 is a cross-sectional view taken along line 18—18 of FIG. 15.
Figure 19:
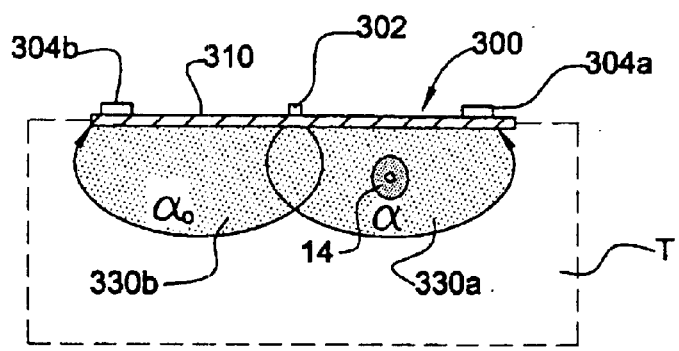
FIG. 19 is a diagrammatic view illustrating the $TQ_a$ hematocrit sensor of FIG. 14 and the illuminated volumes or "glowballs" produced by the emitter and seen by the detectors thereof.

To determine $\alpha_o$, measurements are made in areas 130b and 130c near but not including the access site 14, as depicted, for example, in FIG. 7. If the tissue is more or less homogenous, it is only necessary to make a single reference $\alpha_o$ measurement, using either two emitters 202a and 202b and one detector 204 (as shown in FIG. 13) or one emitter 302 and two detectors 304a and 304b (as shown in FIG. 19), as discussed in greater detail hereinafter. On the other hand, if a gradient in $\alpha_o$ exists in the area of interest (and this is often the case in vivo) multiple measurements are made to establish the nature of the gradient and provide an averaged estimate of $\alpha_o$, using two emitters 102a and 102b and two detectors 104a and 104b, as discussed in greater detail hereinafter in connection with FIGS. 2–6.

Determination of $$\frac{di}{i} = \frac{X_b \cdot \Delta K_b}{\alpha}\left(d - \frac{1}{\alpha}\right), \text{ where } A \approx \alpha, \text{ from equation (4)} \qquad (10)$$

or, $$X_b \cdot \Delta K_b = \frac{\frac{di}{i}\alpha}{\left(d - \frac{1}{\alpha}\right)}$$

The value of $$X_b \cdot \Delta H \cdot C = X_b \cdot \Delta K_b = \frac{\frac{di}{i}\alpha}{\left(d - \frac{1}{\alpha}\right)} \qquad (11)$$

is defined as the time derivative of intensity i, normalized by i. This is expressed as $$\frac{di}{i}$$

wherein $\Delta K_b$ is proportional to $\Delta H$. Hence, $$\frac{di}{i}$$

To determine $$\frac{di}{i} = \frac{I_{baseline} - I(t)}{I_{baseline}} \quad (12)$$

a baseline intensity (taken in the absence of a bolus) is first measured to establish a reference. The intensity is then measured as a time varying signal as the saline bolus is injected, I(t). The quantity $$F\left(\frac{\Delta H}{H}\right)$$

is then calculated as $$F\left(\frac{\Delta H}{H}\right)$$

Final Determination of $$\frac{di}{i}$$

The value $$\frac{di}{i}$$

is the ratio of equations (11) and (8), $$F\left(\frac{\Delta H}{H}\right) = \frac{\frac{di}{i}\alpha}{\left(d - \frac{1}{\alpha}\right)(\alpha^2 - \alpha_0^2)} \quad (13)$$

Since d is fixed and known $$\frac{di}{i},$$

$\alpha$, and $\alpha_o$ are computed by equations (10) and (5). It is important to note that in the final ratio of $$F\left(\frac{\Delta H}{H}\right),$$

the access blood proration value, $X_b$, cancels out. This removes vascular access size, volume, or depth dependence from the final result. Likewise, the $$\frac{di}{i}$$

and $$\frac{\alpha}{\alpha^2 - \alpha_0^2}$$

ratios eliminate skin color variations.

In order to use indicator dilution techniques to measure vascular access flow rates during routine hemodialysis, the indicator must be injected upstream and its concentration detected downstream in the blood flowing through the vascular access site 14. Reversing the dialysis blood lines 16a and 16b during the hemodialysis treatment permits application of indicator dilution by direct injection of the indicator into the dialysis venous tubing 16b. Because the $TQ_a$ sensor 12 can detect a dilution signal downstream of the venous needle 24 through the skin, a unique application of indicator dilution principles permits determination of the vascular access flow rate without reversal of the dialysis blood lines 16a and 16b. Various methods of measuring vascular access blood flow rate, as well as a method for locating accesses and grafts and localizing veins in normal patients, using the $TQ_a$ sensor 12 are described in co-pending U.S. application Ser. No. 09/750,122 (published U.S. application No. US-2002-0128545-A1) entitled "Method of Measuring Transcutaneous Access Blood Flow," filed [on even date herewith, Attorney Docket P65685US0] Dec. 29, 2000, which is incorporated herein in its entirety.

The accuracy of the measurements taken using the $TQ_a$ sensor 12 depends critically on at least two factors. As can be seen in equation (3) above, the calculated access flow rate depends directly on the volume of saline injected; therefore, care must be taken to inject a given amount of saline over a specified time interval. The latter does not need to be known precisely; however, it is important that it be less than approximately 10 seconds to avoid significant interference due to cardiopulmonary recirculation (CPR) of the injected saline. The second factor that is important to consider in the accuracy of the $TQ_a$ measurements is the placement of the $TQ_a$ sensor 12 to accurately determine changes in hematocrit through the skin. The sensor 12 must be placed directly over the vascular access site 14 approximately 25 mm downstream of the venous needle 24 in the specified orientation to accurately determine the relative changes in hematocrit. Additional variability due to sensor placement does not appear, however, to be significant, in that small variations in sensor placement do not significantly influence the measured vascular access flow rate. An additional concern is whether variations in accuracy of measurements taken using the $TQ_a$ sensor 12 may occur with access sites that are not superficial or if the access diameter is very large; however, varying the spacing of sensor elements eliminates difficulties associated with very large accesses or with deeper access sites such as those typically found in the upper arm or thigh. Less accurate results would also be obtained if the sensor 12 does not accurately detect changes in hematocrit due to significant variation in skin pigmentation. The $TQ_a$ sensor in accordance with the invention has been specifically designed to account for the individual absorption and scattering properties of patient tissues, through the use of 805 nm–880 nm LED optical technology, and the normalized nature of the measurements $$\left(\frac{di}{i}\right)$$

suggests that the sensitivity of the calculated vascular access flow rate to skin melanin content is minimal.

Referring now to FIGS. 2–6, there is shown a first embodiment of the $TQ_a$ sensor 100 in accordance with the present invention for the transcutaneous measurement of vascular access blood flow in a hemodialysis shunt or fistula 14. In this embodiment two emitters 102a and 102b and two detectors 104a and 104b are arranged in alignment along an axis A1 on a substrate 110. As mentioned above, this embodiment is employed if a gradient in $\alpha_o$ exists in the area of interest (as is often the case in vivo), as multiple measurements must be made to establish the nature of the gradient and provide an averaged estimate of $\alpha_o$.

The sensor 100 has an access placement line L1 perpendicular to the axis A1. For proper operation, the sensor 100 must be placed with the access placement line L1 over the venous access site (shunt) 14. One of the emitters (the "inboard emitter") 102a and one of the detectors (the "inboard detector") 104a are placed at inboard positions on either side of and equidistant from the access placement line L1. The second emitter (the "outboard emitter") 102b is placed at a position outboard of the inboard detector 104a, while the second detector (the "outboard detector") 104b is placed at a position outboard of the inboard emitter 102a, so that the emitters 102a and 102b and detectors 104a and 104b alternate. The spacing between the emitters 102a and 102b and the detectors 104a and 104b is uniform.

The substrate 110 is provided with apertures 116 in its lower surface (the surface which in use faces the access site 20) for receiving the emitters 102a and 102b and the detectors 104a and 104b. The apertures 116 are sized so that the emitters 102a and 102b and the detectors 104a and 104b lie flush with the lower surface of the substrate 110.

Preferably, the upper surface of the substrate 110 is marked with the access placement line L1. The upper surface of the substrate 110 may also be provided with small projections 120 or other markings above the apertures 116 indicating the locations of the emitters 102a and 102b and the detectors 104a and 104b.

The circuitry (not shown) associated with the emitters 102a and 102b and the detectors 104a and 104b can be provided as a printed circuit on the lower surface of the substrate 110. The substrate 110 is made of a material that is flexible enough to conform to the contours of the underlying tissue but rigid enough to have body durability.

As shown in FIG. 7, there are three illuminated volumes or "glowballs" 130a, 130b, and 130c in the tissue, T, seen by the two detectors 104a and 104b: a first glowball 130a representing the reflective penetration volume ($\alpha$) of the inboard emitter 102a through the access site tissue as seen by the inboard detector 104a in the process of determination of the access Hematocrit; a second glowball 130b representing the reflective penetration ($\alpha_{o1}$) of the inboard emitter 102a through the non-access site tissue that surrounds the access site 14 as seen by the outboard detector 104b; and a third glowball 130c representing the reflective penetration ($\alpha_{o2}$) of the outboard emitter 102b through the non-access site tissue that surrounds the access site 14 as seen by the inboard detector 104a. An estimate of $\alpha_o$ is made by averaging $\alpha_{o1}$ and $\alpha_{o2}$. That is, $$\alpha_o = \frac{\alpha_{o1} + \alpha_{o2}}{2} \quad (14)$$

Due to the depth of the access site 14, in order for the cross-section of the access site 14 to be enclosed by the glowball 130a of the inboard emitter 102a seen by the inboard detector 104a, the spacing between the inboard emitter 102a and the inboard detector 104a is typically 24 mm.

Referring now to FIGS. 8–12, there is shown a second embodiment of the $TQ_a$ sensor 200 in accordance with the present invention. In this embodiment two emitters 202a and 202b and one detector 204 are arranged in alignment along an axis A2 on a substrate 210. As mentioned above, this embodiment is employed if the tissue, T, is more or less homogenous, and it is only necessary to make a single reference $\alpha_o$ measurement.

The sensor 200 has an access placement line L2 perpendicular to the axis A2. One of the emitters (the "inboard emitter") 202a and the detector 204 are placed at inboard positions on either side of and equidistant from the access placement line L2. The second emitter (the "outboard emitter") 202b is placed at a position outboard of the detector 204, so that the emitters 202a and 202b and the detector 204 alternate. The spacing between the emitters 202a and 202b and the detector 204 is uniform.

The substrate 210 is provided with apertures 216 in its lower surface for receiving the emitters 202a and 202b and the detector 204. The apertures 216 are sized so that the emitters 202a and 202b and the detector 204 lie flush with the lower surface of the substrate 210.

Preferably, the upper surface of the substrate 210 is marked with the access placement line L2, and also is marked with "plus" and "minus" signs 218a and 218b, which indicate the direction to move the sensor 200 left or right. The upper surface of the substrate 210 may also be provided with small projections 220 or other markings above the apertures 216 indicating the locations of the emitters 202a and 202b and the detector 204.

The circuitry (not shown) associated with the emitters 202a and 202b and the detector 204 can be provided as a printed circuit on the lower surface of the substrate 210. The substrate 210 is made of a material that is flexible enough to conform to the contours of the underlying tissue but rigid enough to have body durability.

As shown in FIG. 13, there are two illuminated "glowballs" 230a and 230b seen by the single detector 204: a first glowball 230a representing the reflective penetration ($\alpha$) of the inboard emitter 202a through the access site tissue as seen by the single detector 204 in the process of determination of the access Hematocrit; and a second glowball 230b representing the reflective penetration ($\alpha_o$) of the outboard emitter 202b through the non-access site tissue that surrounds the access site 14 as seen by the single detector 204.

Referring now to FIGS. 14–18, there is shown a third embodiment of the $TQ_a$ sensor 300 in accordance with the present invention. The third embodiment is similar to the second embodiment, except that one emitter 302 and two detector 304a and 304b are arranged in alignment along an axis A3 on a substrate 310.

The sensor 300 has an access placement line L3 perpendicular to the axis A3. The emitter 302 and one of the detectors (the "inboard detector") 304a are placed at inboard positions on either side of and equidistant from the access placement line L3. The second detector (the "outboard detector") 304b is placed at a position outboard of the emitter 302, so that the emitter 302 and the detectors 304a and 304b alternate. The spacing between the emitter 302 and the detectors 304a and 304b is uniform.

The substrate 310 is provided with apertures 316 in its lower surface for receiving the emitter 302 and the detectors 3204a and 3204b. The apertures 316 are sized so that the emitter 302 and the detectors 304a and 304b lie flush with the lower surface of the substrate 210.

The circuitry (not shown) associated with the emitter 302 and the detectors 304a and 304b can be provided as a printed circuit on the lower surface of the substrate 310. The substrate 310 is made of a material that is flexible enough to conform to the contours of the underlying tissue but rigid enough to have body durability.

Preferably, the upper surface of the substrate 310 is marked with the access placement line L3, and also is marked with "plus" and "minus" signs 318a and 318b, which indicate the direction to move the sensor 300 left or right. The upper surface of the substrate 310 may also be provided with small projections 320 or other markings above the apertures 316 indicating the locations of the emitter 302 and the detectors 304a and 304b.

As shown in FIG. 19, there are two illuminated "glowballs" 330a and 330b seen by the detectors 304a and 304b: a first glowball 330a representing the reflective penetration ($\alpha$) of the single emitter 302 through the access tissue as seen by the inboard detector 304a in the process of determination of the access Hematocrit; and a second glowball 330b representing the reflective penetration ($\alpha_o$) of the single emitter 302 through the non-access site tissue that surrounds the access site 14 as seen by the outboard detector 304b In the first three embodiments, the placement of the emitters and detectors permits all of the measurements to be made only in tissue volumes perpendicular to the access site 14. There will now be discussed fourth and fifth embodiments, in which the placement of the emitters and detectors permits measurements to be made in tissue areas parallel, as well as perpendicular, to the access site 14.

Figure 20:
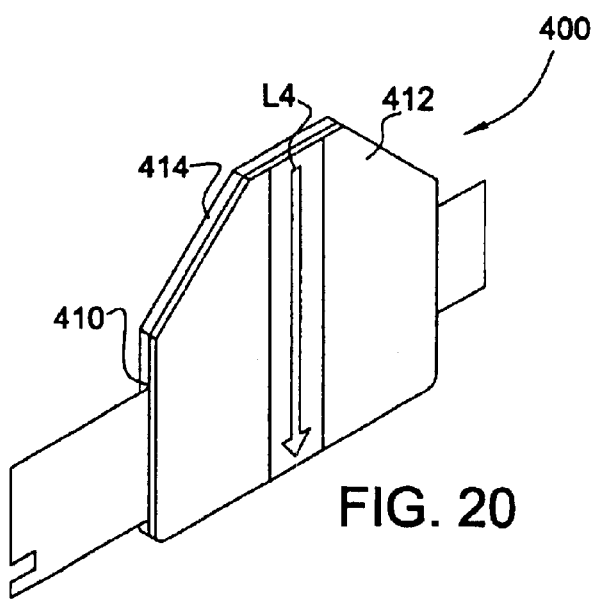
FIG. 20 is a perspective view of a fourth embodiment of a $TQ_a$ hematocrit sensor in accordance with the present invention.
Figure 21:
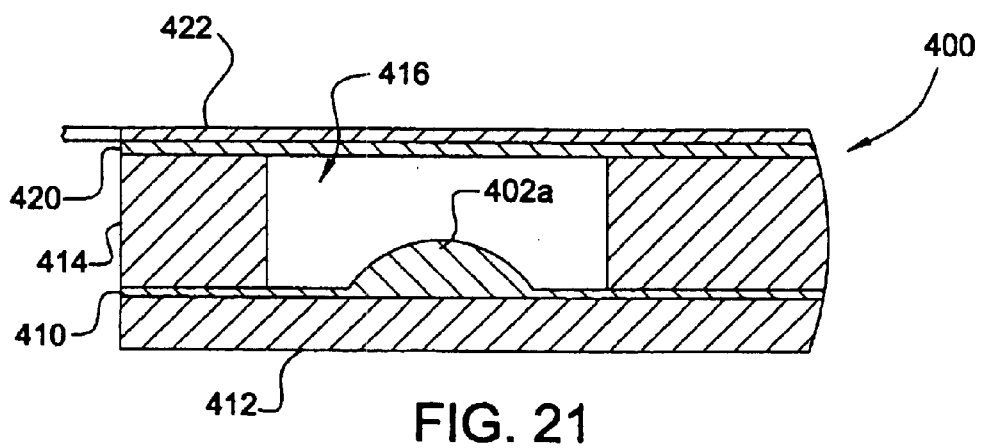
FIG. 21 is a partial cross-sectional view of the $TQ_a$ hematocrit sensor of FIG. 20.
Figure 22:
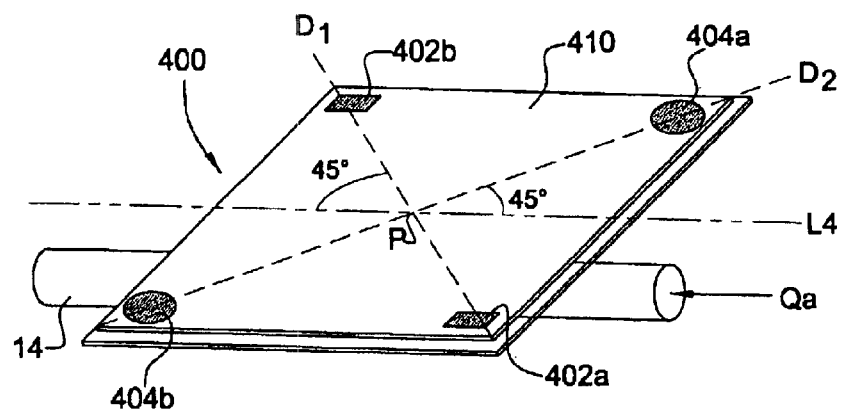
FIG. 22 is a diagrammatic view of the $TQ_a$ hematocrit sensor of FIG. 20 showing the placement of the emitters and detectors relative to the access site.

Referring to FIGS. 20–22, there is shown a fourth embodiment of the $TQ_a$ sensor 400 in accordance with the present invention. In the fourth embodiment, a flexible components layer 410 is provided having an access placement line L4. An upstream and a downstream emitter 402a and 402b are arranged on the components layer 410 along a first diagonal line D1 forming a 45° angle with the access placement line L4, and an upstream and a downstream detector 404a and 404b are arranged along a second line D2 perpendicular to the first line at its point of intersection P with the access placement line L4. The upstream and downstream emitters 402a and 402b and the upstream and downstream detectors 404a and 404b are equidistant from the point of intersection P. It will thus be seen that the upstream emitter 402a and the downstream detector 404b lie on one side of the access placement line L4 along a line parallel thereto, and the upstream detector 404a and the downstream emitter 402b lie on the other side of the access placement line L4 along a line parallel thereto; and that the upstream emitter 402a and the upstream detector 404a lie along a line perpendicular to the access placement line L4, as do the downstream emitter 402b and the downstream detector 404b.

In the $TQ_a$ sensor 400 in accordance with the fourth embodiment, the circuitry associated with the emitters 402a and 402b and the detectors 404a and 404b is also incorporated in the flexible components layer 410. The components layer 410 has a lower surface that faces the access site 14, and an upper surface that faces away. The emitters 402a and 402b and the detectors 404a and 404b may protrude from the lower surface of the components layer 410. A cover layer 412 of flexible foam or the like covers the upper surface of the components layer 410. A spacer layer 414 of flexible foam or the like covers the lower surface of the components layer 410, and has apertures 416 in registration with the emitters 402a and 402b and the detectors 404a and 404b, so that each emitter and detector is received in its own corresponding aperture 416. The spacer layer 414 has an upper surface that contacts the lower surface of the components layer 410 and a lower surface that faces away from the components layer 410.

Preferably, the upper surface of the cover layer 412 is marked with the access placement line L4, and also is marked to indicate which end of the access placement line L4 is to be placed adjacent the venous needle 24, to assist in proper placement. Also, the $TQ_a$ sensor 400 preferably is elongated in the direction of the access placement line L4, in order to ensure the proper placement of the emitters 402a and 402b and the detectors 404a and 404b relative to the venous needle 24.

In order to hold the $TQ_a$ sensor 400 in place, a transparent adhesive layer 420 can be applied to the lower surface of the spacer layer 414. The adhesive can be any suitable pressure sensitive adhesive. A release liner 422 covers the adhesive layer 420. Prior to use, the release layer 424 is removed from the adhesive layer 420 of the $TQ_a$ sensor 400, and the $TQ_a$ sensor 400 is adhered to the access site 14.

Figure 26:
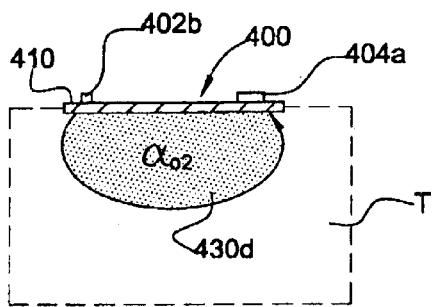

As shown in FIGS. 23–26, there are four illuminated "glowballs" seen by the upstream and downstream detectors: a first glowball 430a representing the reflective penetration ($\alpha$) of the upstream emitter 402a through the access site tissue as seen by the upstream detector 404a in the process of determination of the access hematocrit (FIG. 23); a second glowball 430b representing the reflective penetration ($\alpha$) of the downstream emitter 402b through the access site tissue as seen by the downstream detector 404b in the process of determination of the access Hematocrit (FIG. 24); a third glowball 430c representing the reflective penetration ($\alpha_{o1}$) of the upstream emitter 402a through the non-access site tissue that surrounds the access site 14 as seen by the downstream detector 404b (FIG. 25); and a fourth glowball 430d representing the reflective penetration ($\alpha_{o2}$) of the downstream emitter 402b through the non-access site tissue that surrounds the access site 14 as seen by the upstream detector 404a (FIG. 26). An estimate of $\alpha_o$ is again made by averaging $\alpha_{o1}$ and $\alpha_{o2}$.

Figure 29:
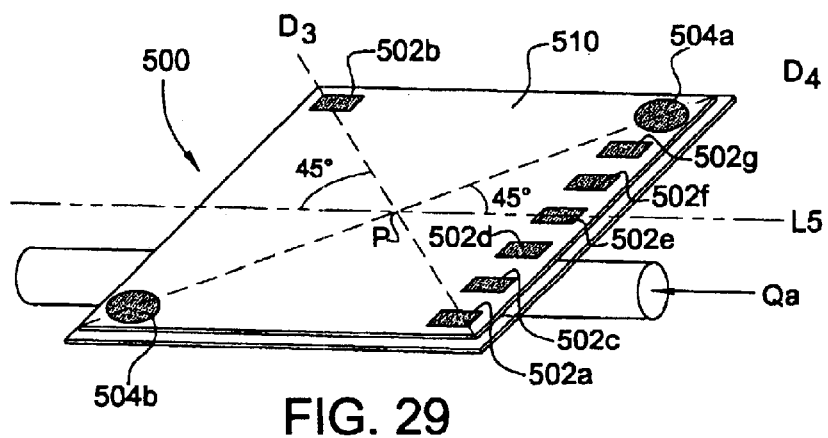
FIG. 29 is a diagrammatic view of the $TQ_a$ hematocrit sensor of FIG. 27 showing the placement of the emitters and detectors relative to the access site.
Figure 23:
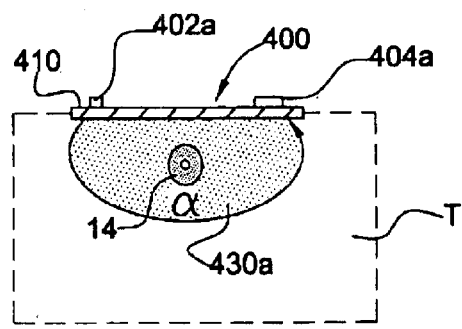
FIGS. 23–26 are diagrammatic views illustrating the $TQ_a$ hematocrit sensor of FIG. 20 and the illuminated volumes or "glowballs" produced by the emitters and seen by the detectors thereof.
Figure 24:
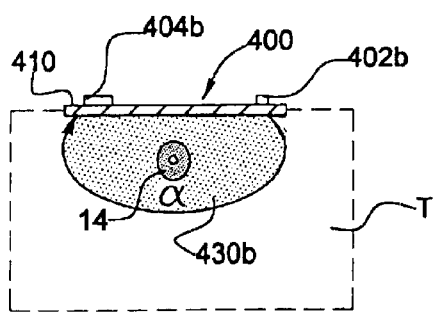
Figure 25:
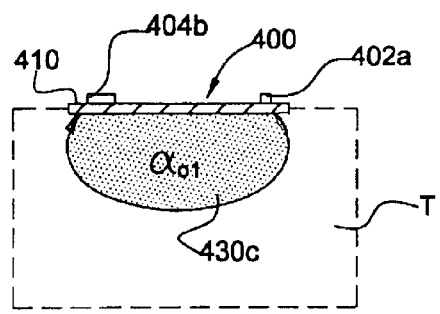
Figure 27:
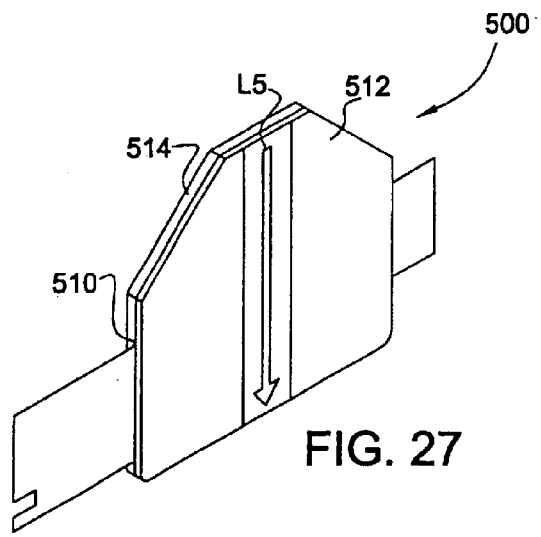
FIG. 27 is a perspective view of a fifth embodiment of a $TQ_a$ hematocrit sensor in accordance with the present invention.
Figure 28:
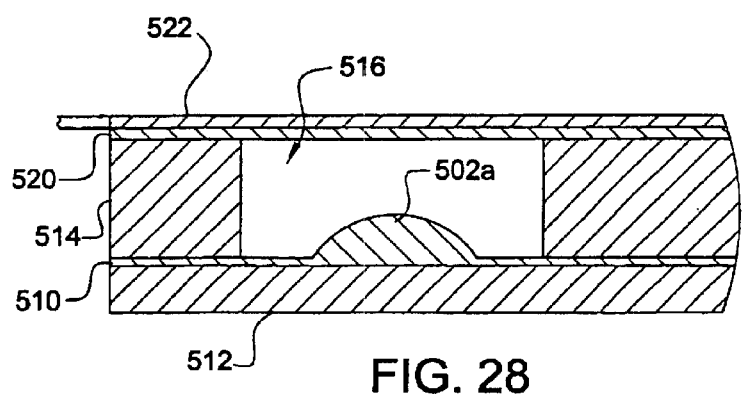
FIG. 28 is a partial cross-sectional view of the $TQ_a$ hematocrit sensor of FIG. 27.

Referring to FIGS. 27–29, there is shown a fifth embodiment of the $TQ_a$ sensor 500 in accordance with the present invention. In the fifth embodiment, a substrate 510 is provided having an access placement line L5. A first upstream emitter 502a and a downstream emitter 502b are arranged on the substrate 510 along a first diagonal line D3 forming a 45° angle with the access placement line L5, and upstream and downstream detectors 504a and 504b are arranged along a second line D4 perpendicular to the first line at its point of intersection P with the access placement line L4, exactly as in the fourth embodiment, with the first upstream and the downstream emitters 502a and 502b and the upstream and downstream detectors 504a and 504b being equidistant from the point of intersection P. In addition, the second, third, fourth, fifth, and sixth upstream detectors 502c, 502d, 502e, 502f, and 502g are arranged in alignment along a line defined by the first upstream emitter 502a and the upstream detector 504a, with the fourth detector 502e lying on the access placement line L5. The second, third, fourth, fifth, and sixth emitters 502c, 502d, 502e, 502f, and 502g are uniformly spaced between the first upstream emitter 502a and the upstream detector 504a and can be used to locate the access. In addition, pairs of emitters 502a and 502c–502g can be used to determine the diameter of the access.

The cover layer 512, spacer layer 514, adhesive layer 522, and release liner 524 of the sensor 500 in accordance with the fifth embodiment are identical to those of the sensor 400 of the fourth embodiment, except that the apertures 516 in the spacer layer 514 will be placed in accordance with the placement of the emitters 502a–502g and the detectors 504a and 504b in the components layer 510 of the fifth embodiment.

Figure 30:
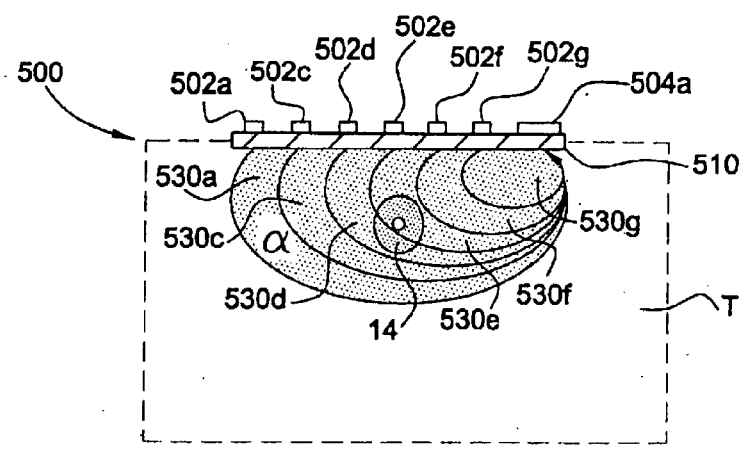
FIGS. 30–33 are diagrammatic views illustrating the $TQ_a$ hematocrit sensor of FIG. 27 and the illuminated volumes or "glowballs" produced by the emitters and seen by the detectors thereof.
Figure 31:
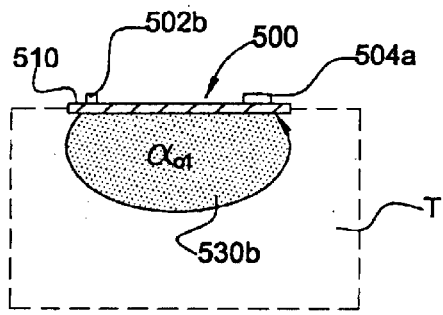

As shown in FIGS. 30 and 31, there are six illuminated glowballs perpendicular to the access site 14 and one illuminated glowball parallel to the access site 14 that are seen by the upstream detector 504a: a first glowball 530a representing the reflective penetration ($\alpha$) of the first upstream emitter 502a through the access site tissue in the process of determination of the access site Hematocrit (FIG.

30); a second glowball 530b representing the reflective penetration ($\alpha_{o1}$) of the downstream emitter 502b through the non-access site tissue that is parallel to the access site 14 (FIG. 31); a third glowball 530c representing the reflective penetration of the second upstream emitter 502c through both non-access and some of the access volume (FIG. 30); a fourth glowball 530d representing the reflective penetration of the third upstream emitter 502d through both non-access and some of the access volume (FIG. 30); a fifth glowball 530e representing the reflective penetration of the fourth upstream emitter 502e through both non-access and some of the access volume (FIG. 30); a sixth glowball 530f representing the reflective penetration of the fifth upstream emitter 502f through non-access the access volume (FIG. 30); and a seventh glowball 530g representing the reflective penetration of the sixth upstream emitter 502g through non-access volume (FIG. 30).

Figure 32:
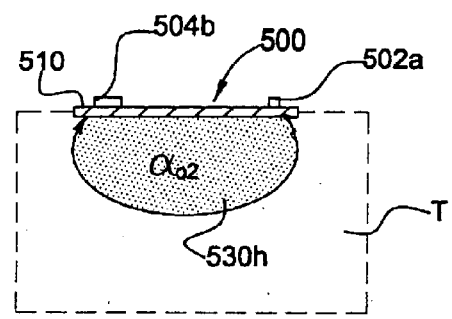
Figure 33:
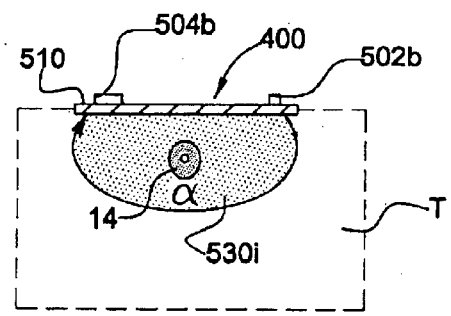

As shown in FIGS. 32 and 33, there are two illuminated "glowballs" seen by the downstream detector 504b: an eighth glowball 530h representing the reflective penetration ($\alpha_{o2}$) of the first upstream emitter 502a through the non-access site tissue that is parallel to the access site 14 (FIG. 32); and a second glowball 530i representing the reflective penetration ($\alpha$) of the downstream emitter 502b through the access site tissue in the process of determination of the access Hematocrit (FIG. 33). An estimate of $\alpha_o$ is made by averaging $\alpha_{o1}$ and $\alpha_{o2}$, and then using equation (13) to determine $$F\left(\frac{\Delta H}{H}\right).$$

Due to the depth of the access site 14, in order for the cross-section of the access site 14 to be enclosed by the glowball of the first upstream emitter 502a seen by the upstream detector 504a, the spacing between the first upstream emitter 502a and the upstream detector 504a is typically 24 mm. The remaining upstream emitters 502c–502g are equally spaced between the first upstream emitter 502a and the upstream detector 504a. Similarly, the spacing between the downstream emitter 502b and the downstream detector 504b are typically 24 mm.

As indicated above, in all of the embodiments, the emitters are preferably LEDs that emit light at a wavelength of 805 nm–880 nm, and the detectors are silicon photodiodes. In the first three embodiments shown in FIGS. 2–6, 8–12, and 14–18, the substrate preferably is provided with an exterior covering (see FIG. 34) of a plastic material, for example urethane or silicone, and the emitters and detectors lie flush with the lower surface of the exterior covering, that is, the surface that faces the skin, so that the emitters and detectors lie on the skin. In the fourth and fifth embodiments shown in FIGS. 20–22 and 27–29, each emitter and detector is recessed in an aperture. The fourth and fifth embodiments use more LED's than the other embodiments.

Also in all of the embodiments, an emitter-detector separation is required so that the reflectance of the first layer of tissue (a non-blood layer of epithelium) does not further exaggerate a multiple scattering effect, as discussed in U.S. Pat. No. 5,499,627, which is incorporated herein by reference in its entirety.

Further, in the all of the embodiments, the distance between each adjacent pair of emitters and detectors must be sufficient for a portion of the access site 14 to be enclosed within the illuminated volume or "glowball" of the inboard emitter. This distance typically is about 24 mm, except as described above with respect to the fifth embodiment.

Figure 34:
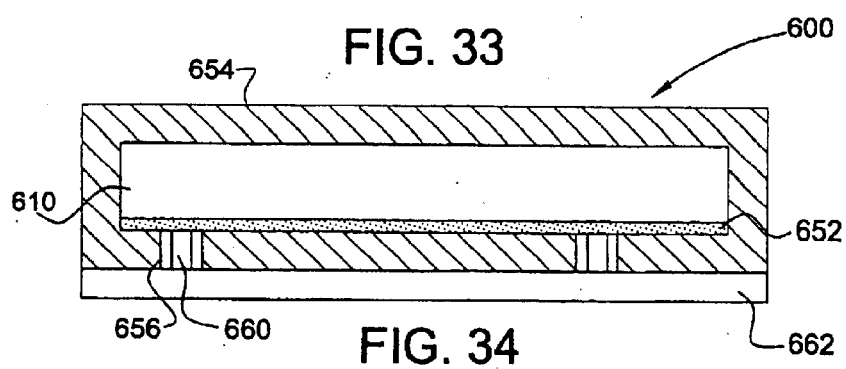
FIG. 34 is a cross-sectional view of a $TQ_a$ hematocrit sensor in accordance with the present invention in the form of a disposable adhesive patch.

Finally, in all of the embodiments, the sensor can be fastened in place using surgical tape. Alternatively, any of the embodiments can be made as a disposable adhesive patch that cannot be recalibrated and used again. Referring to FIG. 34, a sensor 600 includes a substrate 610 that houses a plurality of emitters and detectors (not shown) as previously described, a circuit 652 printed on the skin side of the substrate 610, and an exterior covering 654 covering the circuit 652 and the exposed sides of the substrate 610. The substrate 610 can comprise a flexible material such as MYLAR on which conductive paint has been deposited to define a circuit. Apertures 656 are formed through the skin side of the exterior covering 654 in registration with circuit junctions that are covered by conductive paint that allows continuity across the junctions. Plugs 660 are inserted into the apertures 656 in such a fashion that they adhere to the conductive paint at the circuit junctions. The skin side of the exterior covering 654 is covered by a removable protective layer 662, to which the plugs 660 are also affixed.

Following removal of the sensor 600 from its sterile package and pre-use test and calibration, the protective surface protective layer 662 must be removed in order for the sensor 600 to take a measurement. Because the plugs 660 are adhered to the protective layer 662, when the protective layer 662 is peeled off, the plugs 660 are pulled out of their apertures 656 along with the conductive paint covering the circuit junctions. The circuitry is designed such that once the circuit is broken, the sensor 600 cannot be calibrated again, and can only be used to take one measurement. The sensor 600 thus cannot be re-used.

Operability of the $TQ_a$ sensor in accordance with the invention was confirmed in in vivo tests in 59 hemodialysis patients. Prior to the study dialysis session, a disposable tubing with an injection port (CO-daptoR, Transonic Systems, Ithaca, N.Y., USA) was placed between the venous dialysis tubing and the venous needle. The dialysis circuit was primed with saline in usual fashion taking extra care to remove any air bubbles from the venous injection port.

Within the first hour of dialysis, access recirculation was first measured by the HD01 monitor (Transonic Systems). Then, the dialyzer blood pump was stopped, the dialysis lines were reversed from their normal configuration, and the access blood flow rate was determined, in duplicate, by the HD01 monitor (Transonic Systems). Injection of saline was performed using the saline release method (abstract: Krivitski et al, J Am Soc Nephrol 8:164A, 1997). The dialyzer blood pump was again stopped and the dialysis lines were returned to their normal configuration.

After the dialysis blood lines were returned to the normal configuration and the dialyzer blood pump was restarted, the transcutaneous hematocrit sensor was placed on the skin over the patient's vascular access approximately 25 mm downstream of the venous needle. Thirty ml of normal saline solution were then injected into the injection port of the disposable tubing adjacent to the venous needle at a rate of approximately 300 ml/min to determine access blood flow rate using the $TQ_a$ sensor of the invention. In six patients, saline was injected directly into the arterial dialysis needle before connecting the needle to the complete dialysis circuit. In two patients, saline was injected directly into the access by using a needle and syringe. The data from these various methods were combined together, independent of where saline was injected into the access. The resulting signal proportional to $$\frac{\Delta H}{H}$$

is shown in FIG. 35 with the saline bolus. In 38 patients, this measurement was performed in duplicate to assess the replicability of the method.

All measured and calculated values are reported as mean±SD. The significance of differences in calculated vascular access flow rates determined using the TQa sensor and those determined by the HD01 monitor was determined using a paired Student's t-test. The variability of the slope and intercept from the regression equation is expressed as±the estimated SD (or the SE). The results from the replicability and reproducibility studies are expressed as the average coefficient of variation for the duplicate measurements. P values less than 0.05 were considered statistically significant.

The patients studied were predominantly male and Caucasian; 5 Black and 1 Native American patients were studied. Although the distribution of patient race in the study was not representative of that within the United States as a whole, it was representative of the population in the geographical region where the test was conducted. The age of the patients, the fraction of diabetic patients and the fraction of patients with synthetic PTFE grafts were similar to those for chronic hemodialysis patients in the United States. Eleven patients were studied twice and one patient was studied three times. All other patients were studied once for a total of 72 measurements. Access recirculation was significant in three patients. In those patients, the blood pump setting was reduced to 150 ml/min to eliminate access recirculation before completing the study protocol.

Figure 36:
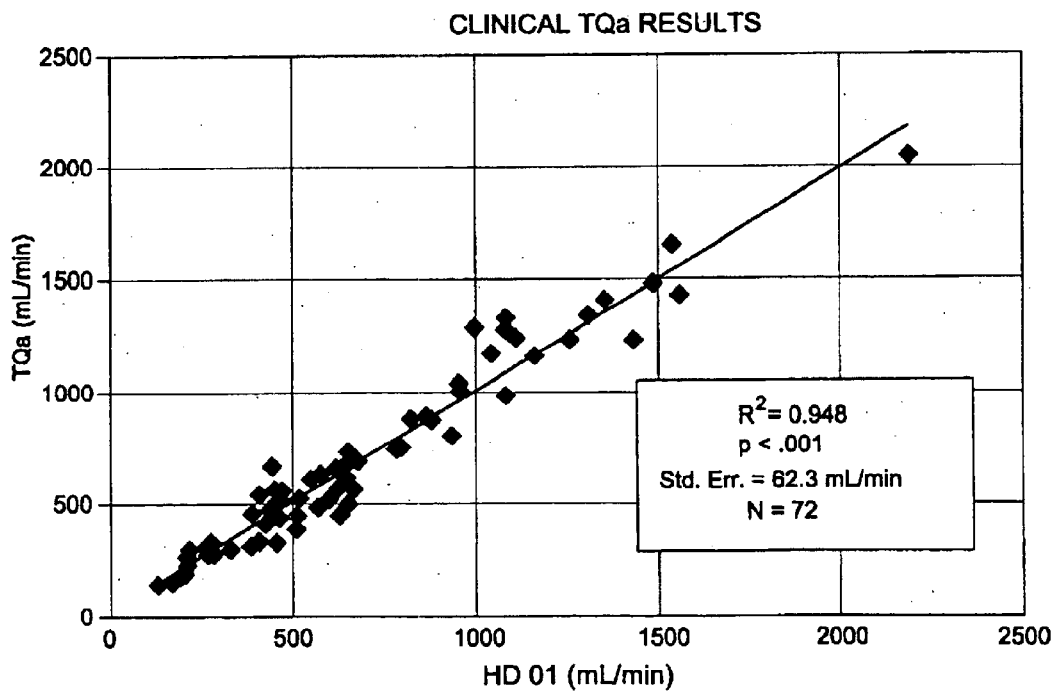
FIG. 36 is a graphical representation of plotted values of the vascular access flow rate determined using a $TQ_a$ sensor in accordance with the present invention versus that determined by a conventional HD01 monitor.

FIG. 36 shows values of the vascular access flow rate determined using the $TQ_a$ sensor plotted versus that determined by the HD01 monitor. The best-fit linear regression line has a slope of essentially unity and a small y-intercept. There was no significant difference between vascular access flow rates determined using the $TQ_a$ sensor and those determined by the HD01 monitor; the mean absolute difference between these methods was 71±63 ml/min. When these results were analyzed for various patient subgroups (male vs. female, black vs. white, diabetic vs. nondiabetic, synthetic grafts vs. native fistulas), excellent agreement between the measured access blood flow rates was similarly observed.

Because the optical $TQ_a$ sensor in accordance with the invention can accurately determine instantaneous changes in hematocrit, it permits use of the bolus injection indicator dilution approach (Henriques-Hamilton-Bergner Principle). This optical approach is likely to be of considerable interest to nephrologists since it is also possible to determine the vascular access flow rate when the patient is in the physician's office or in the clinic and not being treated by hemodialysis by simply injecting saline directly into the access and measuring with a downstream $TQ_a$ sensor. During the initial study, eight patients had vascular access flow rate determinations by direct injection of saline into the access prior to dialysis; their results were later confirmed once the dialysis circuit was in place and functioning. Furthermore, two additional studies were perfored excusively by injecting saline into the access, with excellent results. Thus, it may now be possible to use the $TQ_a$ sensor in accordance with the invention to regularly monitor the vascular access flow rate as an indicator of access function when the patient is not being dialyzed, as well as during maturation of native fistulas prior to first use.

Modifications and variations of the above-described embodiments of the present invention are possible, as appreciated by those skilled in the art in light of the above teachings. For example, the sensor in accordance with the present invention can be used to measure blood constituents other than hematocrit, such as albumen and glucose, in which case the LEDs emit different wavelengths suited to the specific constituent.

Further, the detector-emitter arrangement of the sensor in accordance with the present invention, and in particular of the sensor 110 shown in FIG. 7, allows for precise access location, as a "flow finder," and also can be used to locate grafts and to localize veins in normal patients for more efficient canulatization. In this connection, the sensor 110 is placed directly on the skin over the approximate area of the access, graft, or vein, and values of $\alpha$, $\alpha_{o1}$, and $\alpha_{o2}$ are calculated as described above. A reference ratio, RR, is developed, where:

$$RR = \left(1 - \frac{\alpha_{o1}}{\alpha_{o2}}\right) \times 100$$

When RR<±15, then the access or graft or vein is "centered" correctly or found between the inboard LED 102a and the inboard detector 104a. Also, a signal strength (SS) indicator advises the user whether a sufficient signal is present for an accurate measurement, where $$SS = \left[\left(\alpha - \left(\frac{\alpha_{o1} + \alpha_{o2}}{2}\right)\right)\right] \times 100$$

When SS>40, then a sufficient amount of the access or graft or vein is within the illuminated volume of tissue. If RR is not<±15 (that is, if RR≧±15), or if SS is not>40 (that is, if SS is≦40), then the sensor 110 is moved right or left (+ or −) to find the appropriate spot or location.

It is therefore to be understood that, within the scope of the appended claims and their equivalents, the invention may be practiced otherwise than as specifically described.

What is claimed is:

1. A sensor for the transaction measurement of vascualr access blood for flow comprising:
   a substrate having an axis and an access placement line perpendicular to the axis;
   an inboard emitter and an inboard detector positioned on the substrate on either side of and spaced the same distance from the access placement line; and
   at least one of an outboard emitter and an outboard detector spaced a distance from the inboard detector and the inboard emitter, respectively.

2. The sensor of claim 1, wherein all of the emitters and detectors are collinear and are alternatingly arranged.

3. The sensor of claim 2, wherein the inboard emitter is the only emitter and wherein there is an inboard detector and an outboard detector on either side of the inboard emitter.

4. The sensor of claim 2, wherein the inboard detector is the only detector and wherein there is an inboard emitter and an outboard emitter on either side of the inboard detector.

5. The sensor of claim 2, wherein there is at least one outboard emitter and at least one outboard detector.

6. The sensor of claim 1, wherein all of the emitters are photoemitters that emit light of the same wavelength.

7. A sensor of the transcutaneous measurement of vascular access blood flow, the sensor having an access placement line and comprising:
- a first emitter and a first detector positioned on either side of and space the same distance δ from the access placement line; and
- a second emitter and a second detector positioned on either side of and spaced the same distance δ from the access placement line, the first and second emitters being arranged along a first diagonal line having a point of intersection and forming an angle with the access placement line and the first and second detectors being arranged along a second line at an angle to the first line at the point of intersection with the access placement line.

8. The sensor of claim 7, where the second line is perpendicular to the first line.

9. The sensor of claim 8, wherein the first and second detectors are equidistant from the point of intersection.

10. The sensor of claim 7, wherein all of the emitters are photoemitters that emit light of the same wavelength.

11. A sensor for the transcutaneous measurement of vascular access blood flow, the sensor having an access placement line and comprising:
- a first emitter and a first detector positioned on either side of and spaced the same distance δ from the access placement line; and
- a plurality of additional detectors arranged in alignment along a line defined by the first emitter and the first detector.

12. The sensor of claim 11, wherein one of the additional detectors lies on the access placement line.

13. Apparatus for non-invasively measurement one or more blood parameters associated with a vascular access site, comprising:
- means for optically measuring a blood parameter in a volume of tissue parallel to and excluding the access site; and
- means for optically measuring the blood parameter in a volume of tissue perpendicular to and including at least a portion of the access site.

* * * * *